(12) United States Patent
Longenbach et al.

(10) Patent No.: US 10,384,206 B2
(45) Date of Patent: Aug. 20, 2019

(54) APPARATUS AND METHOD FOR ANALYTE EXTRACTION

(71) Applicant: Waters Technologies Corporation, Milford, MA (US)

(72) Inventors: Pamela J. Longenbach, Northborough, MA (US); Moon Chul Jung, Arlington, MA (US); Frank John Marszalkowski, Jr., Cumberland, RI (US)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 0 days.

(21) Appl. No.: 14/434,316

(22) PCT Filed: Sep. 25, 2013

(86) PCT No.: PCT/US2013/061512
§ 371 (c)(1),
(2) Date: Apr. 8, 2015

(87) PCT Pub. No.: WO2014/058615
PCT Pub. Date: Apr. 17, 2014

(65) Prior Publication Data
US 2015/0266019 A1   Sep. 24, 2015

Related U.S. Application Data

(60) Provisional application No. 61/711,452, filed on Oct. 9, 2012.

(51) Int. Cl.
| | | |
|---|---|---|
| *B01D 35/00* | (2006.01) | |
| *B01L 3/00* | (2006.01) | |
| *G01N 30/06* | (2006.01) | |
| *G01N 1/40* | (2006.01) | |

(52) U.S. Cl.
CPC .............. *B01L 3/5082* (2013.01); *B01L 3/502* (2013.01); *G01N 1/4055* (2013.01); *G01N 30/06* (2013.01); *B01L 2200/0631* (2013.01); *B01L 2300/047* (2013.01); *B01L 2300/0609* (2013.01); *B01L 2300/069* (2013.01); *B01L 2300/0618* (2013.01); *B01L 2300/0681* (2013.01); *B01L 2300/087* (2013.01); *B01L 2300/0832* (2013.01); *B01L 2300/105* (2013.01); *B01L 2400/0457* (2013.01); *B01L 2400/0478* (2013.01); *G01N 2001/4061* (2013.01); *G01N 2030/062* (2013.01)

(58) Field of Classification Search
CPC ........... B01L 3/0217; B01L 2300/0681; G01N 1/405; G01N 1/14

USPC ........................... 422/921, 923, 535
See application file for complete search history.

(56) References Cited

U.S. PATENT DOCUMENTS

| | | | | |
|---|---|---|---|---|
| 4,327,745 | A | * 5/1982 | Ford, Jr. | ............ A61B 5/15003 600/578 |
| 4,572,210 | A | * 2/1986 | McKinnon | .......... A61M 5/3145 600/578 |
| 2004/0029259 | A1* | 2/2004 | McDevitt | ............... B82Y 30/00 506/7 |
| 2004/0069076 | A1* | 4/2004 | Gamble | .................. G01N 1/38 73/863.85 |
| 2005/0227269 | A1 | 10/2005 | Lloyd et al. | |
| 2012/0103421 | A1 | 5/2012 | Grenz et al. | |
| 2013/0017545 | A1 | 1/2013 | Yong et al. | |
| 2013/0116597 | A1 | 5/2013 | Rudge et al. | |
| 2014/0038172 | A1 | 2/2014 | De La Rosa et al. | |
| 2014/0058615 | A1 | 2/2014 | Hatch et al. | |

FOREIGN PATENT DOCUMENTS

| | | |
|---|---|---|
| WO | 2009012808 A1 | 1/2009 |
| WO | 20100102061 A1 | 9/2010 |
| WO | 2011076859 A1 | 6/2011 |
| WO | 2011153122 A2 | 12/2011 |
| WO | 2012067619 A1 | 5/2012 |
| WO | 2013067520 A1 | 5/2013 |
| WO | 2013148071 A1 | 10/2013 |

OTHER PUBLICATIONS

International Search Report & Written Opinion in counterpart international patent application No. PCT/US13/61542, dated May 21, 2014; 12 pages.
European Search Report in counterpart European Application No. 13846024.1, dated Oct. 5, 2018; 8 pages.
Extended European Search Report in counterpart European Application No. 13846024.1, dated Jul. 20, 2016; 12 pages.

* cited by examiner

*Primary Examiner* — Natalia Levkovich
(74) *Attorney, Agent, or Firm* — Schmeiser, Olsen & Watts LLP

(57) ABSTRACT

Described is a matrix spot processing device comprising a tubular apparatus. An absorbent media is located either separate from, or attached to, the tubular apparatus. A sample is spotted on the absorbent media. A reservoir is in the tubular apparatus. A first region of the reservoir is constructed and arranged to have an extraction solvent. A second region of the reservoir, which may or may not be the same as the first region, is constructed and arranged to receive an extract generated from an interaction between the extraction solvent and the spotted sample at the absorbent media.

36 Claims, 17 Drawing Sheets

APPARATUS AND METHOD FOR ANALYTE EXTRACTION

RELATED APPLICATION

This application claims the benefit of and priority to U.S. provisional application No. 61/711,452, filed Oct. 9, 2012, entitled "APPARATUS AND METHOD FOR ANALYTE EXTRACTION," the entirety of which is incorporated by reference herein.

FIELD OF THE INVENTION

The present inventive concepts relate generally to preparing biological fluids such as dried blood spots (DBS) for analysis. More particularly, the present inventive concepts relate to a method and device for spotting biological fluids, and drying, storing, and extracting dried matrix spots at the device.

BACKGROUND

DBS sampling is a technique for collecting blood samples from an animal or human subject and spotting them onto a collection card. In order to extract and analyze the blood samples, a section of each spot is punched out from the collection card. An analyte of interest can be extracted from the DBS using a solvent such as methanol and provided to a vial, well, or other container. An aliquot of the extract can be subsequently provided to analytical measurement equipment such as a liquid chromatographic (LC) system.

SUMMARY

In one aspect, provided is a matrix spot processing device, comprising a tubular apparatus, an absorbent media, and a reservoir in the tubular apparatus. A sample is spotted on the absorbent media. The absorbent media is positioned in the tubular apparatus. A first region of the reservoir is constructed and arranged to have an extraction solvent. A second region of the reservoir is constructed and arranged to receive an extract generated from an interaction between the extraction solvent and the spotted sample at the absorbent media.

In another aspect, provided is a matrix spot processing device comprising a tubular apparatus. The tubular apparatus has a first end and a second end opposite the first end. Each of the first end and the second end has an opening. The device further comprises a fluid path between the opening at the first end and the opening at the second end with a reservoir in the tubular apparatus between the first end and the second end. An absorbent media is positioned at the first end. A sample is spotted on the absorbent media. An extraction solvent is received via the opening at the first end. The extraction solvent is transferred through the absorbent media along the fluid path to the reservoir to generate an extract.

In another aspect, provided is a matrix spot processing device, comprising a tubular apparatus, an attachment mechanism at an inner sidewall at the tubular apparatus, and an absorbent media coupled to the attachment mechanism in the tubular apparatus. A sample is spotted on the absorbent media. The tubular apparatus is constructed and arranged to generate an extract from an interaction between an extraction solvent and the spotted sample at the absorbent media.

In another aspect, provided is a method for processing a matrix spot, comprising: positioning an absorbent media in a tubular apparatus; spotting a sample on the absorbent media; constructing and arranging a first region of the tubular apparatus to have an extraction solvent; and receiving, at a second region of the tubular apparatus, an extract generated from an interaction between the extraction solvent and the spotted sample at the absorbent media.

BRIEF DESCRIPTION OF THE DRAWINGS

The above and further advantages of this invention may be better understood by referring to the following description in conjunction with the accompanying drawings, in which like numerals indicate like structural elements and features in the various figures. For clarity, not every element may be labeled in every figure. The drawings are not necessarily to scale, emphasis instead being placed upon illustrating the principles of the invention.

DETAILED DESCRIPTION

Reference in the specification to "one embodiment" or "an embodiment" means that a particular, feature, structure or characteristic described in connection with the embodiment is included in at least one embodiment of the teaching. References to a particular embodiment within the specification do not necessarily all refer to the same embodiment.

The present teaching will now be described in more detail with reference to exemplary embodiments thereof as shown in the accompanying drawings. While the present teaching is described in conjunction with various embodiments and examples, it is not intended that the present teaching be limited to such embodiments. On the contrary, the present teaching encompasses various alternatives, modifications and equivalents, as will be appreciated by those of skill in the art. Those of ordinary skill having access to the teaching herein will recognize additional implementations, modifications and embodiments, as well as other fields of use, which are within the scope of the present disclosure as described herein.

Figure 1:
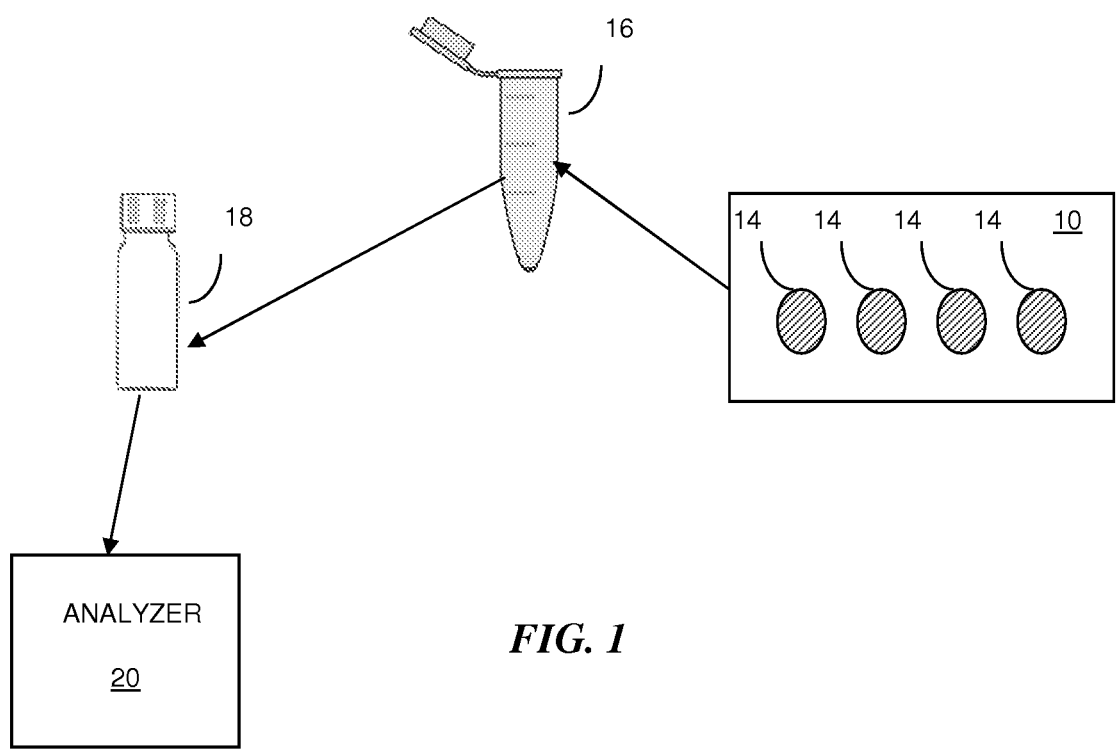
FIG. 1 is a diagram illustrating a conventional DBS workflow process.

FIG. 1 is a diagram illustrating a conventional DBS workflow process. One or more blood spot samples 14 can be provided on a specially manufactured card 10 formed of an absorbent media, commonly referred to as a DBS card. The blood can be air dried on the DBS card. Subsequently, some or all of one or more blood spot samples 14 can be punched from the DBS card 10, and transferred to an extraction tube 16 such as a micro-centrifuge tube or the like. The separated DBS sample 14 can be placed into a solvent to extract the DBS components, including at least one analyte of interest from the dried sample. Here, the DBS sample 14 can be mixed with an extraction solvent such as methanol and optionally diluted with water to extract analytes of interest for analysis. The DBS sample and solvent can be shaken, vortexed, and/or subjected to sonication such as ultrasonic energy to improve the efficiency of the extraction process. The mixture can be centrifuged prior to transfer to a vial or container 18, where an aliquot can be injected or otherwise loaded into an analyzer 20 such as an analytical measurement system such as a high performance liquid chromatography (HPLC) system, an ultra-performance liquid chromatography (UPLC) system and/or a mass spectrometer.

Conventional DBS techniques as shown in FIG. 1 require several time-consuming, error-prone steps that require the transfer of the blood sample to different devices, namely: the spotting, drying, and punching of the blood sample at a DBS card, the transfer of the punched DBS sample to an extraction tube, the addition of extraction solvent, the mixing and centrifuging of the mixture at the extraction tube, the transfer of an aliquot of the extract to another vial, and the injection of the aliquot to an analyzer. Also, analytes may disperse non-uniformly on the DBS card 10. A well-known issue is that the spatial distribution of the analyte can vary significantly with location within a DBS and the concentration of the analyte near the edge of the DBS is often substantially less than the concentration in the central region. In some instances, the presence of the analyte is irregular such that there are small regions with little or no concentration of the analyte. Also, since blood samples of varying hematocrits can produce spots of various sizes, a same size punch from DBS spots of varying hematocrits can contain varying amounts of blood and an associated analyte. In general, a punched portion of a spot used for analysis may not be representative of the entire blood spot sample. Moreover, particular attention is required during the punch process to ensure that the DBS card is accurately punched at the location of the DBS. Otherwise, an inaccurate punch can result in the DBS sample lacking in uniformity. Also, information available from the original blood sample can be lost in the extraction process or during transfers between the card 10, the extraction tube 16, and the vial 18.

Embodiments of the present inventive concepts are directed to a system and method that rely on a single device for spotting, drying, storing, shipping, filtering, extracting, and/or centrifuging a biological sample for analysis, such as a blood, plasma, urine, saliva, or cerebrospinal fluid sample. The feature of the present inventive concepts obviates the need to punch a blood spot that has dried on a DBS card, and the transfer of a punched DBS to a different container for extraction. In this manner, conventional issues regarding the extraction of only a portion of a spotted blood sample are eliminated, since an entire spot is processed.

In an embodiment, a blood sample or other biological fluid is spotted on a surface of an absorbent media located inside a tube, vial, or other small container, or alternatively, at the end of a plunger device for insertion into an extraction tube, a storage cap, or related container. After the blood spot has dried, an extraction technique can be applied to the dried sample in the container.

Figure 2:
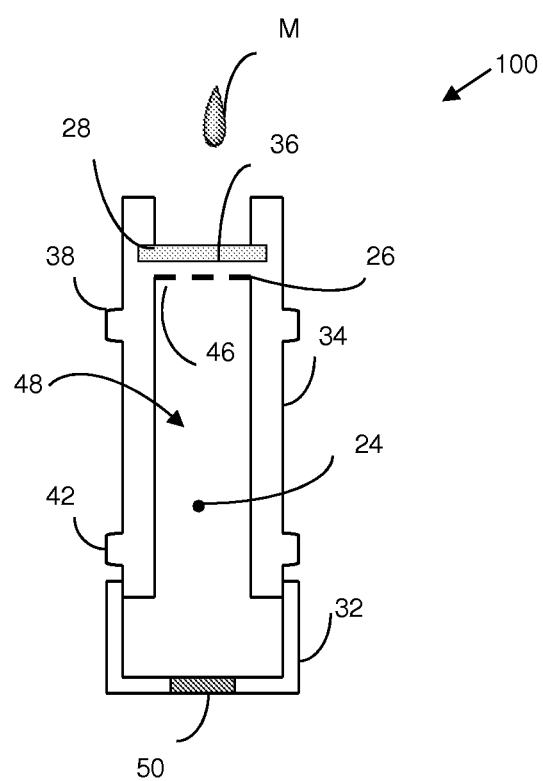
FIG. 2 is a cutaway front view of a plunger of a matrix spot processing device, in accordance with an embodiment.

FIG. 2 is a cutaway front view of a plunger 34 of a matrix spot processing device 100, in accordance with an embodiment.

The plunger 34 preferably includes a tubular or cylindrical configuration. A first end of the plunger 34 includes an absorbent media 36. A second end of the plunger 34 opposite the first end can include a cap 32. The first end of the plunger 34 is constructed and arranged to hold an absorbent media 36 in place, and for providing a collection region for a biological matrix, which can be spotted, dried, and stored in the absorbent media 36, and extracted from the absorbent media 36 for analysis. The absorbent media 36 can be positioned at a groove 28 about at least a portion of a perimeter of an inner sidewall of the plunger 34. Alternatively, the absorbent media 36 can be secured in position by a lip, a mount, or other related protrusion that extends from the inner wall of the plunger 34.

The absorbent media 36 can be a commercially available biological matrix paper such as a Guthrie card. Alternatively, the absorbent media 36 can have other configurations, for example, a square, rectangular, elliptical, parabolic, or other 3-dimensional shape.

A dried matrix spot such as a DBS can be extracted at a reservoir 48 in the plunger 34, eliminating extra steps associated with cutting a sample from a DBS card and manually depositing the cut sample in separate tube or vial containing an extraction solvent. The spotting region can be established by the area of the absorbent media 36. Because the entire spot of blood located on the absorbent media 36 is extracted, any issues of obtaining inaccurate results due extracting a punched-out portion of the dried blood spot are eliminated. Conventional approaches associated with punching a DBS card containing a matrix spot, on the other hand, can result in the inaccurate measurement of analytes.

One or more openings or channels 46 can extend between the absorbent media 36 and the reservoir 48 at a region 26 of the plunger 34. In this manner, the plunger 34 can be inserted into a container (for example, the container 52 shown in FIG. 3) that holds an extraction solvent or other liquid (not shown in FIG. 2). In doing so, when the plunger 34 is pressed into the container, the extraction fluid can be forced through the absorbent media 36 and the openings 46 into the reservoir 48 of the plunger 34. The plunger 34 can include an air vent 24 that removes air from the reservoir 48 when the plunger 34 is pressed into the container 52.

As described above, a removable cap 32 can be positioned at an opposite end of the plunger 34 as the absorbent media 36. The plunger 34 can include a thread (not shown in FIG. 2) so that the cap 32 can be screwed against the plunger 34. Alternatively, the same end of the plunger 34 can have a lip, flanges, or the like extending from the outer surface of the plunger 34, permitting the cap 32 to be snap-fit to the plunger 34. The cap 32 can include a pierceable and/or pre-slit septum 50 for removing an aliquot from the reservoir 48 of the plunger 34. The septum 50 can be pierced with a pipette, syringe needle, or other related sharp object. The septum 50 can be formed of silicone or other materials known to those of ordinary skill in the art.

Figure 3:
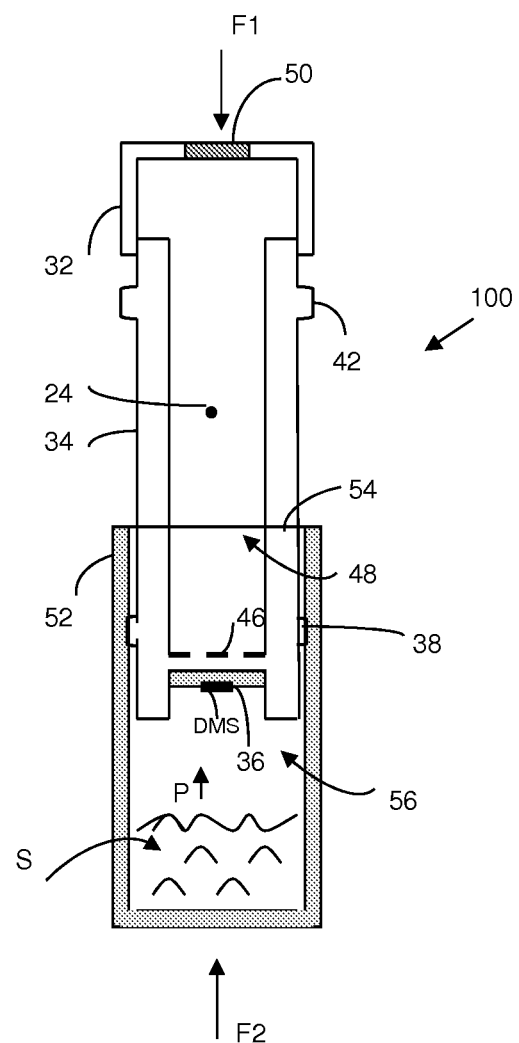
FIG. 3 is a cross-sectional view of a matrix spot processing device including the plunger of FIG. 2 in communication with an extraction solvent container, in accordance with an embodiment.

The matrix spot processing device 100 can include a first seal 38 about the plunger 34 to provide a fluid-tight seal between the outer surface of the plunger 34 and an inner surface of a container, for example, container 52 shown in FIG. 3, into which the plunger 34 is positioned. The first seal 38 can be integral with, and extend directly from, an outer surface of the plunger 34, for example, a lip. Alternatively, the first seal 38 can be formed separately from, and be attached to, the outer surface of the plunger 34, for example, a seal ring. The first seal 38 can be formed of compliant, deformable materials The matrix spot processing device 100 can include a second seal 42 that likewise provides a fluid-tight seal between the outer surface of the plunger 34 and an inner wall of a container into which the plunger 34 is positioned. The second seal 42 can be on an opposite side of the air vent 24 as the first seal 38. The second seal 42 can be integral with, and extend directly from, an outer surface of the plunger 34, for example, a lip. Alternatively, the second seal 42 can be formed separately from, and be attached to, the outer surface of the plunger 34. The second seal 42 can be formed of compliant, deformable materials During operation, the plunger 34 can be inverted as shown in FIG. 2 to expose the absorbent media 36 to an operator. Blood or other biological fluid can be spotted on the absorbent media 36, which can be subsequently dried and processed, for example, extracted for analysis. Fluid samples can be spotted by an operator in a manner that requires less dexterity and precision, since the absorbent media 36 extends from a table surface, the height determined by the length of the plunger 34. A conventional DBS card on the other hand requires greater dexterity and precision with respect to spotting a location on the DBS card, which lies flat on a table.

FIG. 3 is a cross-sectional view of a matrix spot processing device 100 including the plunger 34 of FIG. 2 in communication with an extraction solvent container 52, in accordance with an embodiment. The plunger 34 can be the same as or similar to the plunger 34 shown in FIG. 2. Details of the plunger 34 are therefore not repeated for reasons related to brevity.

Figure 4:
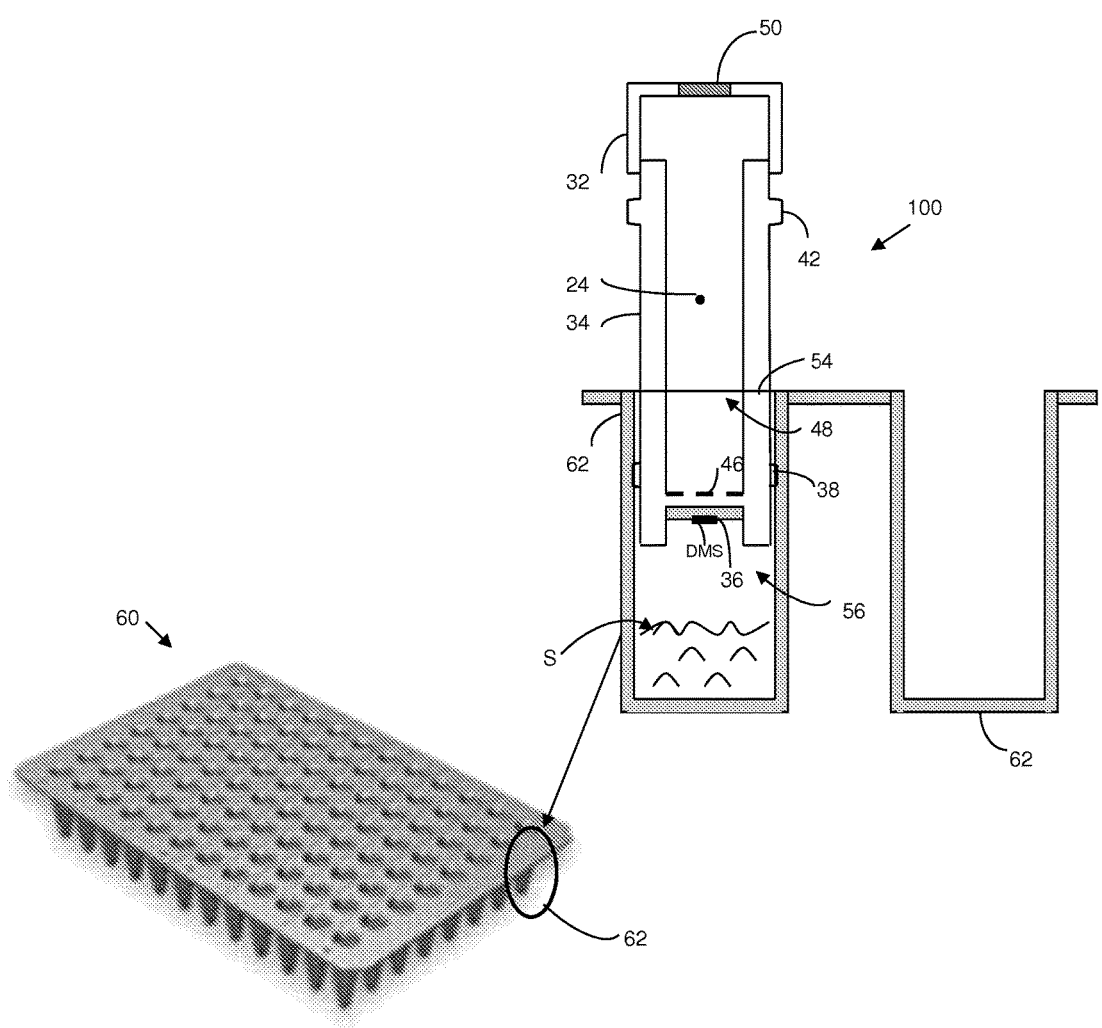
FIG. 4 is a cross-sectional view of a matrix spot processing device including a plunger in communication with a well plate, in accordance with an embodiment.

The extraction solvent container 52 can be a vial or other tubular apparatus, for example, a micro-centrifuge tube. Alternatively, as shown in FIG. 4, the plunger 34 can be constructed and arranged for communicating with a well 62 of a well plate 60. The well plate 60 can include an array, i.e., rows and columns, of wells 62, each capable of receiving a plunger 34 in accordance with embodiments of the present inventive concepts, for example, described herein.

The extraction solvent container 52 includes an opening 54 that can receive the plunger 34. At least a portion of the plunger 34 can be inserted into the opening 54, where the plunger 34 is presented to a reservoir 56 that holds an extraction solvent. The reservoir 56 of the container 52 can be at least partially filled with an extraction solvent S. The solvent S can include methanol, acetonitrile, or water, with or without additives to enhance analyte extraction.

Following the operation described at FIG. 2, the first end of the plunger 34, i.e., the end proximal the absorbent media 36, can be inserted at the opening 54 of the container 52. A force F1 can be applied to the plunger 34 and/or a force F2 can be applied to the container 52 to compress the plunger 34 into the container 52. The first seal 38 and/or the second seal 42 of the plunger 34 can provide fluid-tight seals between the outer surface of the plunger 34 and the inner wall of the container 52. Materials such as fluids, gases, and the like can be prevented from leaking through an interface formed by the seal(s). When a force F1 and/or F2 is applied in this manner, a distance between the absorbent media 36 and the bottom of the container is reduced such that at least a portion of the extraction solvent interacts with the sample to form the extract in the reservoir 48 of the plunger 34. In this manner, a pressure P in the sealed container reservoir 56 can cause at least some of the extraction solvent 56 to be transferred from the container reservoir 56 to the plunger reservoir 48 of the plunger 34 through the absorbent media 36 having the dried matrix spot. Accordingly, an extract can be generated from an interaction between the dried matrix spot and the extraction solvent S, and transferred to the plunger reservoir 48.

Figure 5:
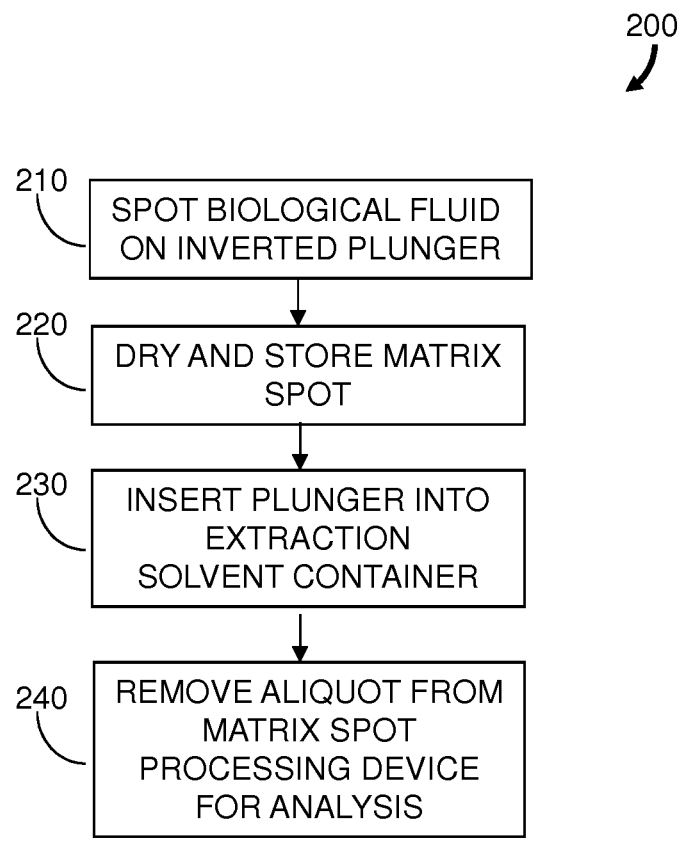
FIG. 5 is a flow diagram illustrating a method for preparing a biological fluid for analysis, in accordance with an embodiment.

FIG. 5 is a flow diagram illustrating a method 200 for preparing a biological fluid for analysis, in accordance with an embodiment. In describing the method 200, reference is made to elements of FIGS. 2-4.

At block 210, a sample of a biological fluid M is spotted at an end of a plunger 34 in an inverted position. The biological fluid can include blood, plasma, urine, saliva, cerebrospinal fluid, and so on, or a combination thereof. A sample of the biological fluid, for example, 3 microliters of a blood sample, can be dropped, pipetted, injected, or otherwise placed onto an absorbent media 36, which is positioned at the end of the plunger 34.

At block 220, the biological fluid sample is dried on the absorbent media 36 in the plunger 34 to form a dried matrix spot.

At block 220, the dried matrix spot is stored at the plunger 34. The dried matrix spot on the absorbent media 36 can be sealed within the walls of the plunger 34 by placing a cap over the opening of the matrix spot processing device 100, for example, shown in FIG. 6.

At block 230, the plunger 34 is inserted into a container 52 having an extraction solvent S. A fluid path is formed between the container reservoir 56 on one side of the absorbent media 36 and the plunger reservoir 48 on the other side of the absorbent media 36.

At block 240, an extraction is performed on the dried matrix spot. More specifically, the dried matrix spot can be reconstituted in an extraction solvent S provided from the container reservoir 56 for later analysis such as a liquid chromatographic tandem mass spectrometric (LC-MS) assay. During an extraction process, the plunger 34 can be pressed into the container 52 until the extraction solvent S in the container 52 is transferred through the absorbent media 36 to the plunger reservoir 48. The matrix spot processing device 100 can also undergo vortexing, shaking, and/or sonication, or other mixing techniques that contribute to an interaction between the dried matrix spot and the extraction solvent. As a result, some or all of the constituents of the dried matrix spot in a volume of extraction solvent S can be acquired to produce an extract. The volume of extraction solvent S for creating an extract from the dried matrix spot DMS can be determined based on an estimated quantity of an analyte of interest.

The extract can be subsequently provided to an analytical measurement system. In one embodiment, the solvent container 52 combined with the matrix spot processing device 100 containing the extract can be inserted into an autosampler device or related apparatus. An aliquot of the extract can be drawn from the plunger reservoir 48 by a needle or pipette inserted through the septum 50 to the reservoir 48. In another embodiment, the drawn extract can be placed into a separate vial, tube, or other container for injection to an instrument for analysis, such as a UPLC or HPLC system, for example, to analyze one or more analytes of interest in the dried sample spot.

The abovementioned extraction process can be performed on an absorbent media such as a Guthrie card or the like to which a predetermined amount of a blood sample, for example, 3 microliters, is spotted. Here, the entire blood spot can be extracted and analyzed. Recovery and matrix effect results using embodiments of the present inventive concepts to prepare DBS samples for analysis can be similar to those obtained when applying a conventional whole spot method of DBS sample preparation. For example, results averaged across 10 analytes can give, with the matrix spot processing device 100, an average of an 88% recovery and a root-mean-square of 6% matrix effect, while the corresponding results from a conventional whole spot method are an 87% recovery and a 4% matrix effect.

During either the whole spot or the traditional punched spot method of preparing dried blood spots for analysis, the blood sample is transferred between three different devices: (1) the DBS card or the device holding the spotted prepunched disk, (2) the container used for extraction, and (3) the container used for injection. The matrix spot processing device 100 and/or other devices according to embodiments herein are unique in that a single container can be used for the entire sample preparation, which minimizes transfer errors and simplifies the process, while maintaining the advantages of a whole spot method over the traditional punched spot method. Both the punched spot and whole spot methods can take up to five steps to prepare the sample, including the steps of punching and/or transferring the spotted punch to the extraction vial, adding the extraction solvent, extracting, centrifuging, and transferring the extract to an injection vial. On the other hand, embodiments of the present inventive concepts require two steps to prepare the sample for injection: (1) adding an extraction solvent to the container, and (2) placing the spotted plunger into the container. Because the devices and methods in accordance with embodiments herein rely on fewer steps to prepare the dried blood spot for analysis, the risk of error is reduced, and less time is required.

Figure 6:
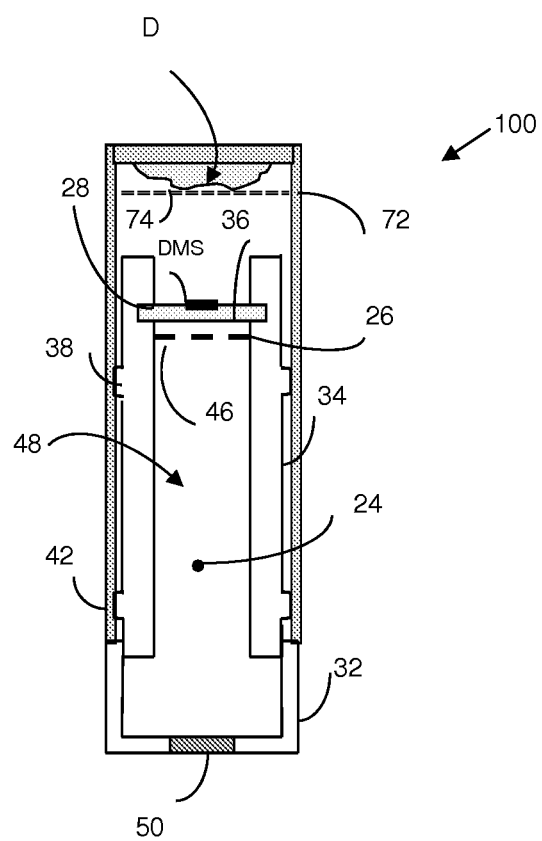
FIG. 6 is a cross-sectional view of a storage cap positioned on a matrix spot processing device, in accordance with an embodiment.

FIG. 6 is a cross-sectional view of a storage cap 72 positioned on a matrix spot processing device 100, in accordance with an embodiment. The storage cap 72 can be positioned at the distal end of the plunger 34 of the device 100 shown in FIG. 2, in an inverted position. Therefore, details of the plunger 34 are not repeated for brevity.

The plunger 34 can be inserted in an opening of the storage cap 72. A fluid-tight interface can be formed between the storage cap 72 and the plunger 34, for example, by the second seal 42 of the plunger 34. The storage cap 72 can be in positioned over the first seal 38. In this manner, the dried matrix spot DMS on the plunger 34 is sealed from the outside atmosphere.

The storage cap 72 can include a screen 74 or other surface having openings for holding a desiccant, which can reduce or eliminate moisture buildup, permitting the dried matrix spot DMS to be stored and transported to a laboratory or other location. The desiccated storage of the dried matrix spot DMS can provide stability with respect to analytes in the sample.

Figure 7:
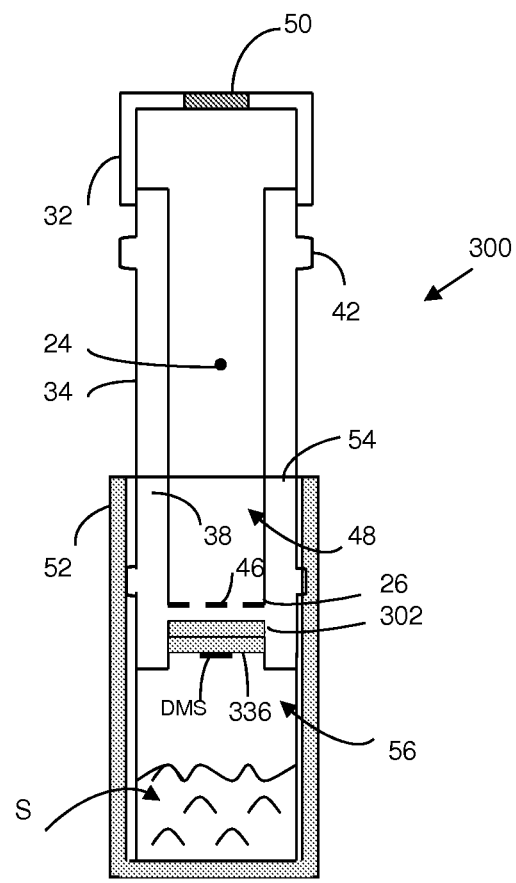
FIG. 7 is a cutaway front view of a matrix spot processing device, in accordance with an embodiment.

FIG. 7 is a cutaway front view of a matrix spot processing device 300, in accordance with an embodiment. The matrix spot processing device 300 can be similar to the matrix spot processing device 100 described with reference to FIGS. 2-6, except that the matrix spot processing device 300 includes a filtration media 302 collocated with an absorbent media 336.

In a preferred embodiment, the filtration media 302 is sandwiched between the absorbent media 336 and a bottom region 26 of the plunger 34. This permits a user to spot a biological fluid on the absorbent media 336 instead of the filtration media 302. The filtration media 302 can filter a fluid, for example, an extraction solution, simultaneously with a force F1, F2 being applied to the plunger 34 and/or the container 52, for example, shown in FIG. 3. The extraction solution can pass through the absorbent media 336 and the filtration media 302 to the plunger reservoir 48, while preventing particulates and the like too large to pass through the filtration media 302. Particulates or other impurities having a particular size can therefore be separated from the resulting filtered extract in the plunger reservoir 48. The filtered extract can subsequently be analyzed in accordance with embodiments described herein.

Figures 8A, 8B:
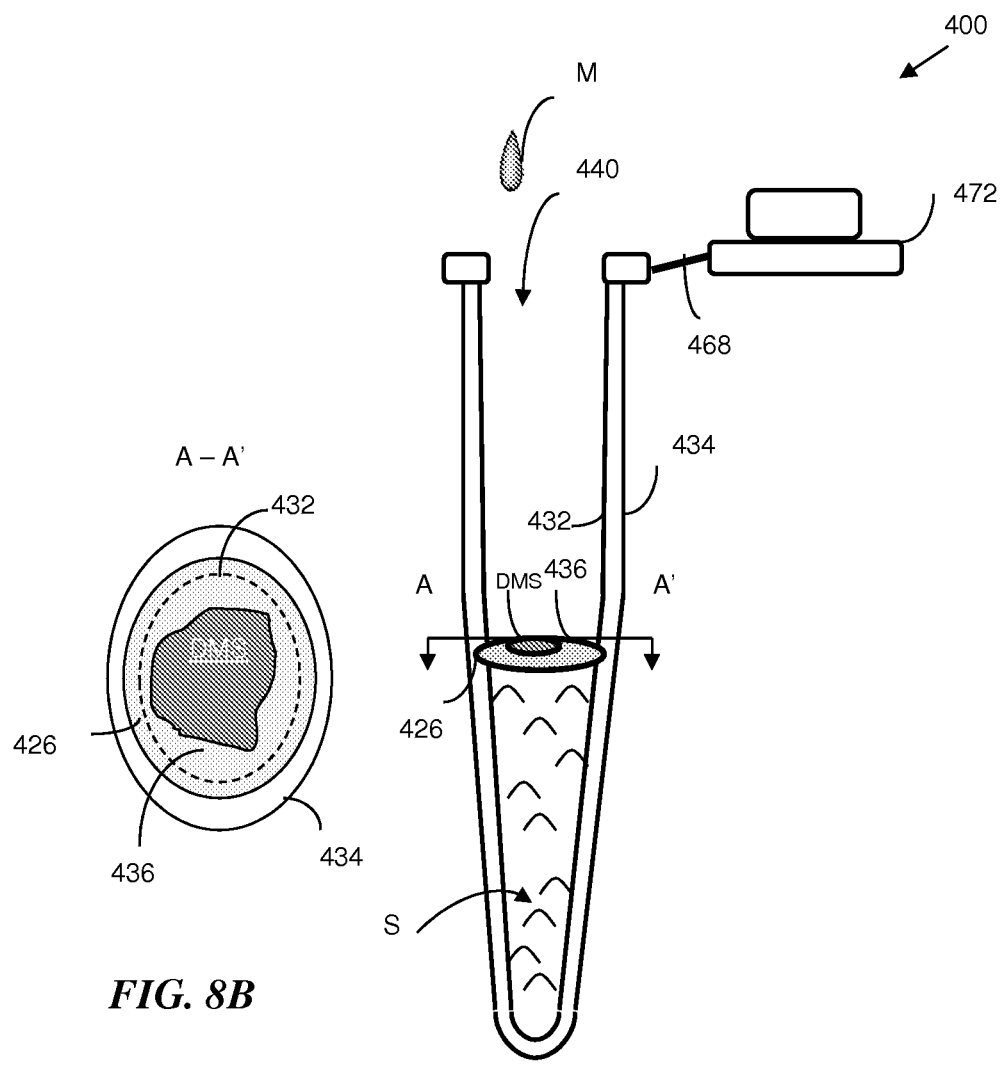
FIG. 8A is a cutaway front view of a matrix spot processing device, in accordance with another embodiment.
FIG. 8B is a cross-sectional top view of the matrix spot processing device of FIG. 8A, taken along line A-A' of FIG. 8A.

FIG. 8A is a cutaway front view of a matrix spot processing device 400, in accordance with an embodiment. FIG. 8B is a cross-sectional top view of the matrix spot processing device 400 of FIG. 8A, taken along line A-A' of FIG. 8A.

The matrix spot processing device 400 can include a tube 434, or vial, or related apparatus have a tubular or cylindrical configuration. For example, the matrix spot processing device 400 can have a shape of a micro-centrifuge tube. A first end of the device 400 includes an opening to a chamber 440. An absorbent media 436 is positioned in the chamber 440. A biological matrix M can be spotted onto the absorbent media 436. In one embodiment, the biological matrix M is spotted on the absorbent media 436 while it is located within the tube 434. In another embodiment, the biological matrix M is spotted on the absorbent media 436 prior to insertion of the absorbent media 436 in the tube 434. The biological matrix M can also be dried and stored at the chamber 440, and extracted from the chamber 440 for analysis. An inner wall 432 of the chamber 440 can include a groove 426 for holding the absorbent media 436 in position in the chamber 440. As shown in FIG. 8, a groove 426 can extend about at least a portion of a perimeter of an inner wall 432 of the chamber 440. Alternatively, the absorbent media 436 can be secured against the inner wall 432 by a lip, mount, support, or other restraining device. Alternatively, or in addition, a lip or the like can extend from the inner wall 432, and the absorbent media 436 can be positioned on the lip or the like. A defined volume can be formed from the inner wall 432 of the chamber 440 and the absorbent media 436, permitting whole spot sampling to occur at the absorbent media 436, which can reduce or eliminate punching and hematocrit inaccuracies.

The absorbent media 436 can be a commercially available biological matrix paper such as a Guthrie card. The absorbent media 436 can have other shapes instead of a disk-shape, for example, a square, rectangular, elliptical, parabolic, or other 3-dimensional shape.

The matrix spot processing device 400 can include a cap 472. The cap 472 can be coupled to the device 400 by a hinge 468 or other connection mechanism. The cap 472 can include a container (not shown) for holding a desiccant or the like, which can reduce or eliminate moisture buildup, permitting the dried matrix spot DMS to be stored and transported to a laboratory or other location.

The dried matrix spot DMS can be extracted at the device 400 by generating an extract from an interaction between the dried matrix spot and the extraction fluid S. The device 400 can be shaken, vortexed, and/or subjected to sonication such as ultrasonic energy to improve the efficiency of the extraction process. Centrifuging can occur at the device 400 to dislodge the absorption media 436 from the groove 426, lip, or other attachment, allowing for extract to be removed directly from the device 400. For example, a portion of the extract can be transferred to another container for injection or injected from the device 400 into an LC or other analysis system.

Figure 9:
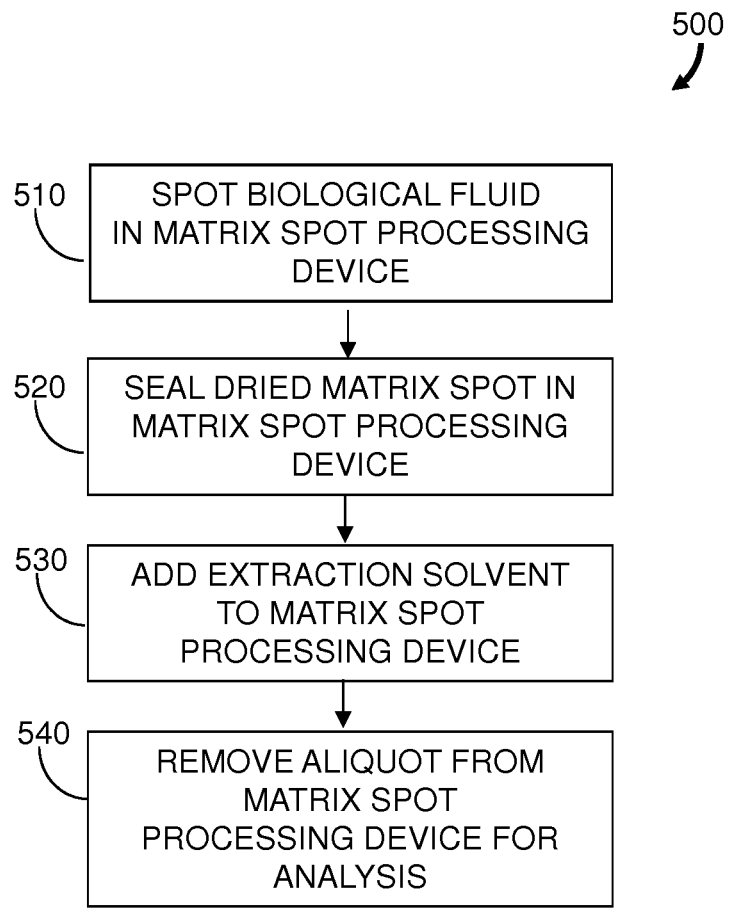
FIG. 9 is a flow diagram illustrating a method for preparing a biological fluid for analysis, in accordance with an embodiment.

FIG. 9 is a flow diagram illustrating a method 500 for preparing a biological fluid for analysis, in accordance with an embodiment. In describing the method 500, reference is made to elements of FIG. 8.

At block 510, a biological fluid is spotted at an absorbent media 436 positioned in a matrix spot processing device, for example, the matrix spot processing device 400 shown and described with respect to FIG. 8. The biological fluid can include blood, plasma, urine, saliva, cerebrospinal fluid, or a combination thereof. A sample of the biological fluid can be pipetted, injected, or otherwise placed onto an absorbent media 436. The sample can be placed on the absorbent media 436 either before the absorbent media 436 is positioned in the chamber 440 of the device 400, or while the absorbent media 436 is located in the chamber 440. The biological fluid sample can be dried at the absorbent media 436 in the matrix spot processing device 400. The dried biological fluid sample can be referred to as a dried matrix spot.

At block 520, the dried matrix spot on the absorbent media 436 can be sealed in the matrix spot processing device 400, more specifically, the chamber 440, by placing a cap 472 over the opening of the matrix spot processing device 400. The cap 472 can be constructed and arranged to provide a fluid-tight seal about the opening, to prevent liquid or gas from escaping the chamber 440.

At block 530, an extraction solvent can be added to the matrix spot processing device 400. The extraction solvent can at least partially fill the chamber 440 until the absorbent media 436 is partially or completely submerged in the extraction solvent. The volume of extraction solvent S for creating an extract from the dried matrix spot DMS can be determined based on an estimated quantity of an analyte of interest.

After the extraction solvent is added to the matrix spot processing device 400, the matrix spot processing device 400 can undergo vortexing, shaking, and/or sonication, or other mixing techniques that contribute to an interaction between the dried matrix spot and the extraction solvent. As a result, some or all of the constituents of the dried matrix spot in a volume of extraction solvent S can be acquired to produce an extract.

At block 540, an aliquot of the extract can be drawn from the chamber 440, for example, by a needle or pipette. The drawn extract can be placed into a separate vial, tube, or other container for injection to an instrument for analysis, such as a UPLC or HPLC system, for example, to analyze one or more analytes of interest in the dried matrix spot. In another embodiment, the matrix spot processing device 400 containing the extract can be inserted into an autosampler or related device for injection into an instrument for analysis. In another embodiment, the matrix spot processing device 400 can be exposed to centrifuging, for example, to dislodge the absorption media 436 from the groove 426, lip, or other attachment, allowing for injection and the like to occur at device 400 instead of a different vial, tube, and the like.

Figures 10A, 10B:
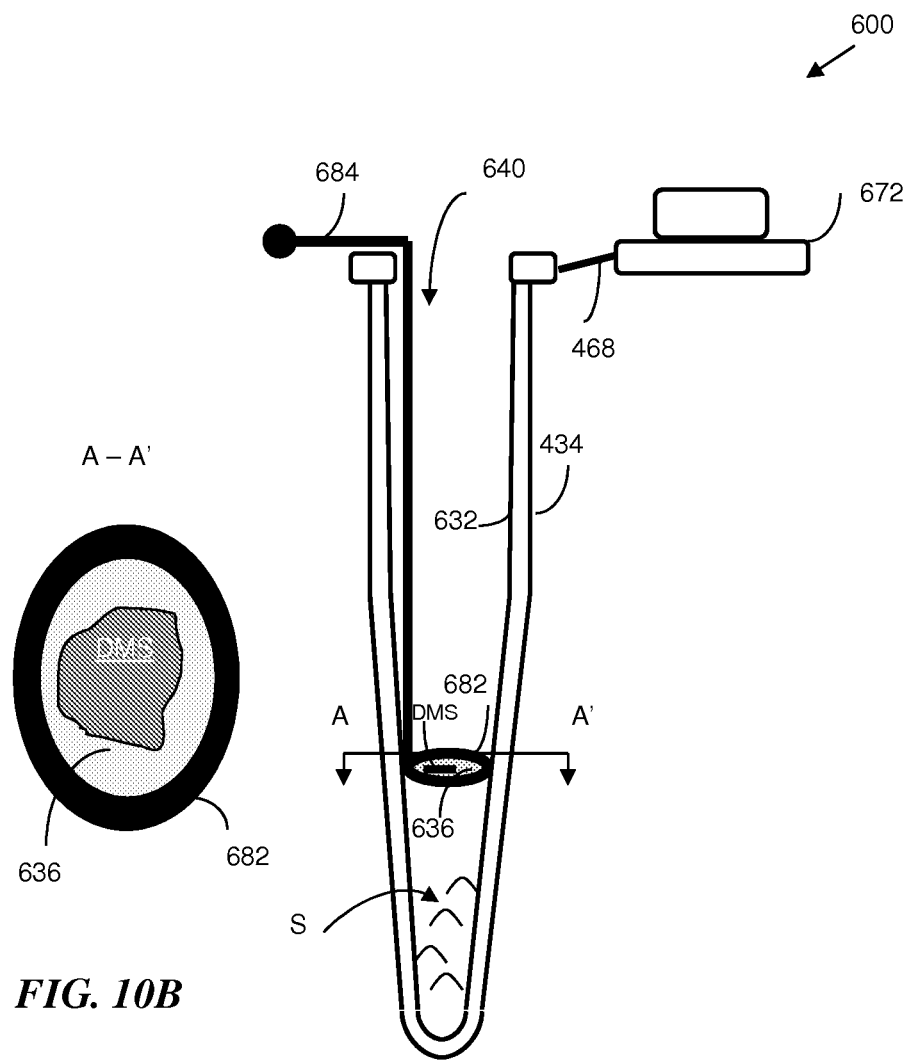
FIG. 10A is a cutaway front view of a matrix spot processing device, in accordance with another embodiment.
FIG. 10B is a cross-sectional top view of the matrix spot processing device of FIG. 10A, taken along line A-A' of FIG. 10A.

FIG. 10A is a cutaway front view of a matrix spot processing device 600, in accordance with another embodiment. FIG. 10B is a cross-sectional top view of the matrix spot processing device 600 of FIG. 10A, taken along line A-A' of FIG. 10A. The matrix spot processing device 600 can be similar to the matrix spot processing device 400. Certain physical details of the matrix spot processing device 600 are therefore not repeated for reasons related to brevity.

A first end of the device 600 includes an opening to a chamber 640. A support ring 682 containing a dried matrix spot DMS is positioned in the chamber 640. The support ring 682 can be attached to a periphery of an absorbent media 636. A biological matrix M can be spotted and dried at the absorbent media 636, then transferred to and stored at the chamber 640, and extracted from the chamber 640 for analysis. The support ring 682 can, but does not need to, abut an inner wall 632 of the chamber 640 such that the support ring 682 is surrounded by a volume of the chamber 640. A defined volume of blood can be spotted on the absorbent media 636, which can be positioned in the inner wall 632 of the chamber 640, and which can be extracted, which can reduce or eliminate punching and hematocrit inaccuracies.

The absorbent media 636 can be a commercially available biological matrix paper such as a Guthrie card. The absorbent media 636 can have other shapes instead of a disk-shape, for example, a square, rectangular, elliptical, parabolic, or other 3-dimensional shape. The support ring 682 can have a different shape than a ring shape to accommodate the shape of the absorbent media 636.

The matrix spot processing device 600 can include a cap 672. The cap 672 can be similar or the same as the cap 472 or other caps described herein. Details of the cap 672 or the hinge 468 will therefore not be repeated for brevity.

The matrix spot processing device 600 can include a support device 684 that is attached to the support ring 682 and extends from the device 600 for simplifying the removal of the support ring 682 and attached absorbent media 636 from the device 600. The support device 684 can be long and rigid, for example, rod-shaped, and can be formed of metals, plastics, composites, or other materials known to those of ordinary skill in the art. The support device 684 can extend from the support ring 682 in a direction of extension of the device 600. In this manner, an end of the support device 684 can extend from the opening of the device 600 so that a user can remove the support ring 682 from the device 600 and/or insert the support ring 682 into the device 600.

During operation, a biological matrix can be spotted at the absorbent media 636. The matrix can be dried and transferred to the chamber 640 for storage. An extraction solvent S can be added to the chamber 640 until the absorbent media 636 is partially or completely submerged in the extraction solvent. Mixing, vortexing, and so on can take place so that analytes of the dried matrix spot DMS are added to the extraction solvent. The support ring 682 can be removed from the chamber 640. In this manner, aliquots of the extract can be removed directly from the device 600. For example, a portion of the extract can be injected from the device 600 into an LC or other analysis system.

Figure 11:
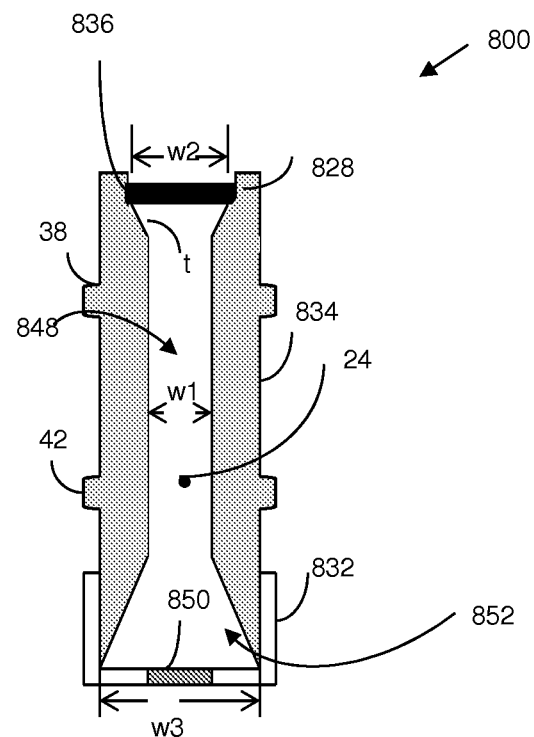
FIG. 11 is a cutaway front view of a matrix spot processing device, in accordance with another embodiment.

FIG. 11 is a cutaway front view of a matrix spot processing device 800, in accordance with another embodiment. The matrix spot processing device 800 is similar to the matrix spot processing device 100 of FIGS. 2-6, except that the matrix spot processing device 800 has a different internal geometry. More specifically, the dimensions of the reservoir 848 can be different than those of matrix spot processing device 100 of FIGS. 2-6.

The reservoir 848 can have a first width (w1) that is less than a second width (w2) at a first end of the device 800. Although a width is referred to throughout the description of FIG. 11, other dimensions such as diameter, circumference, and area can equally apply. The inner wall of the device 800 can include a taper (t) between the first width (w1) of the reservoir 848 and the second width (w2). The first end of the device is constructed and arranged to hold an absorbent media 836 in place, for example, via a groove or other attachment mechanism similar to that described with reference to FIGS. 2-6.

A second end of the device 800 opposite the first end can include a cap 832. The cap 832 and/or the second end of the device 800 can include a funnel 852 that transitions a thickness of an inner wall from a third width (w3) to the first width (w1). A septum 850 can be positioned in the cap 832.

The geometries referred to at FIG. 11 include a smaller diameter of the reservoir 848 that corresponds to a reduced amount of extraction solvent S received at the reservoir of the matrix spot processing device 800 relative to a length of the reservoir. The first width (w1) permits a smaller volume of fluid to accommodate a taller column of the fluid. The taller column relative to the smaller volume of liquid allows more of the fluid to be available to an autosampler for injection into an analyzer such as an HPLC. When a smaller volume is used, the concentration of the analytes in the extract is greater, providing more sensitivity. In this manner, a lesser amount of extraction fluid at the reservoir 848 can permit a greater sensitivity to be obtained with respect to sample analysis.

Figure 12:
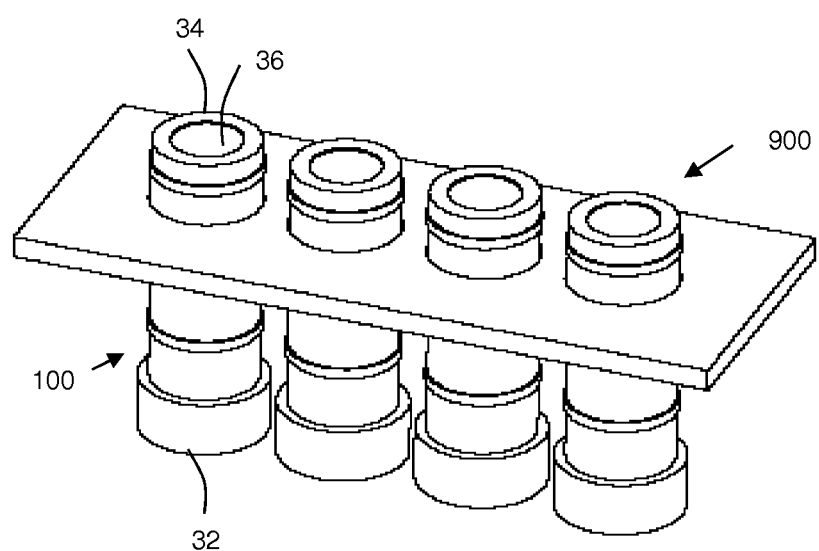
FIG. 12 is a perspective view of a support structure for holding a plurality of matrix spot processing devices, in accordance with an embodiment.

FIG. 12 is a perspective view of a support structure 900 for holding a plurality of matrix spot processing devices, in accordance with an embodiment. Although matrix spot processing devices 100 are referred to in FIG. 12, the support structure 900 can hold one or more of the matrix spot processing devices described with respect to other embodiments illustrated at FIGS. 2-11, for example, device 400 illustrated at FIGS. 8A and 8B.

The matrix spot processing devices 100 can be bundled together similar to a conventional DBS card, for example, four exposed absorbent media 36 in a linear arrangement. The support structure 900 can hold four devices, each having a blood sample from the same patient. An analyst can analyze two or three of the matrix spots, and save the remaining spots in the arrangement for additional processing, for example, Incurred Sample Reanalysis (ISR). Any of the devices 100 can be removed from the support structure 900 for extraction, analysis, or other purposes. In an embodiment, a linear arrangement of devices 100 positioned in a support structure 900 can permit a single cap to be positioned over all of the devices 100. The cap can include a desiccant, for example, similar to that shown and described with respect to FIG. 6. Accordingly, the desiccant can be used for the matrix spots in each of the devices 100 in the support structure 900.

Figure 13:
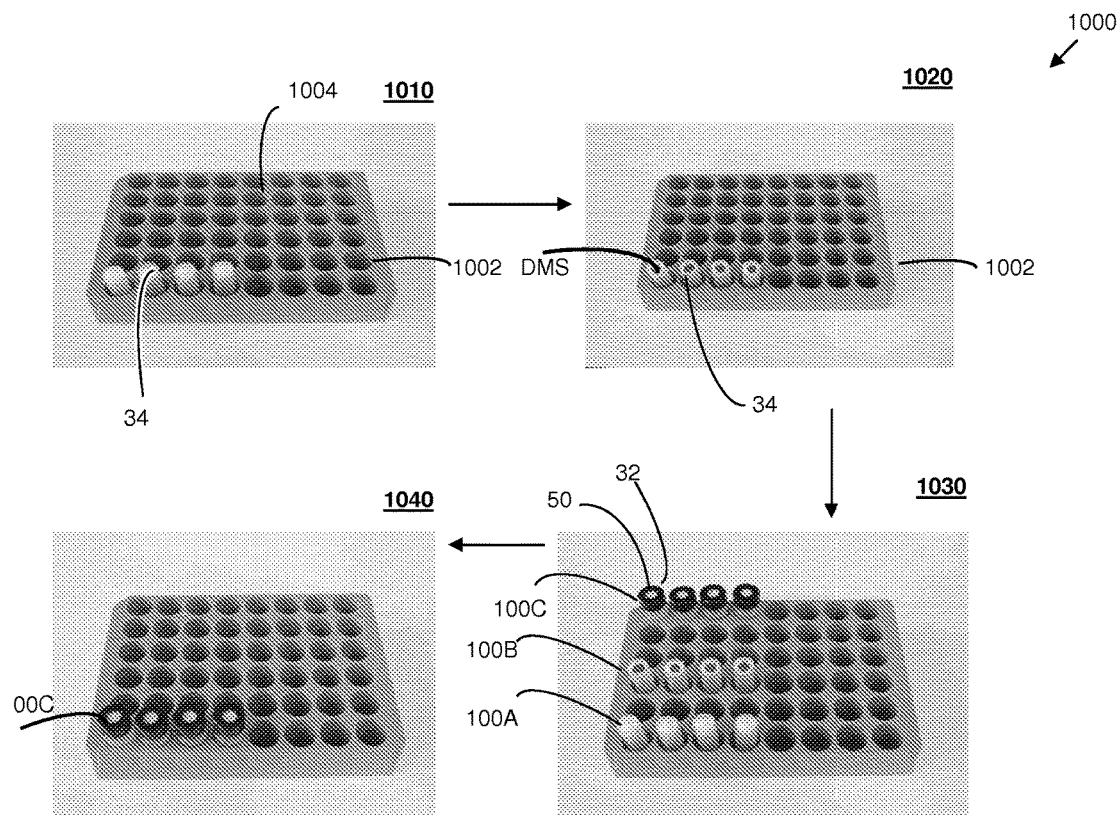
FIG. 13 is a diagram illustrating a dried matrix spot workflow process, in accordance with an embodiment.

FIG. 13 is a diagram illustrating a dried matrix spot workflow process 1000, in accordance with an embodiment.

As shown in illustration 1010, a plurality of plungers 34, each corresponding to a matrix spot processing device, are in an inverted position and inserted in a tray 1002. The tray 1002 includes a plurality of holes 1004. The holes 1004 can be arranged in an array of rows and columns. Each hole 1004 can be constructed and arranged to receive and hold in place a plunger 34 of a matrix spot processing device. Each plunger 34 includes an absorbent media 36 at a first end and a cap (not shown) at a second end. The cap and at least a portion of the plunger 34 are inserted in the tray 1002.

A feature is that a plurality of plungers 34 can be grouped together, and correspond to a same biological fluid, for example, blood from the same person. Some or all of the plungers 34 can be covered with a storage cap, for example, shown and described with respect to FIG. 6.

As shown in illustration 1020, a biological fluid such as blood is spotted on an absorbent media in the plunger 34.

As shown in illustration 1030, three rows of matrix spot processing devices 100A, 100B, 100C (generally, 100) can be provided. The first row can include one or more plungers 34 of the devices 100A positioned similar to that shown in illustration 1010, namely, plungers 34 in an inverted position and inserted in a tray 1002. The second row includes matrix spot processing devices 100B that have been spotted with a biological fluid such as blood, similar to illustration 1020. The plungers 34 of the second row of matrix spot processing devices 100B can each be positioned in a container (not shown), for example, container 52 described herein. The containers 52 can have an extraction solvent. An extract can be generated from an interaction between the extraction solvent and the dried matrix spot in the plunger 34, for example, in accordance with descriptions provided herein. The third row of matrix spot processing devices 100C each includes a plunger 34 and a container (not shown), positioned so that the cap 32 having a septum 50 is exposed from the tray 1002.

Illustration 1040 refers to the matrix spot processing devices 100C, which are moved to a different row in the tray 1002. While in the upright position, at least some of the extract can be withdrawn from the plunger 34 by a pipette, needle, and the like inserted through the cap 32 with a septum 50.

Figure 14:
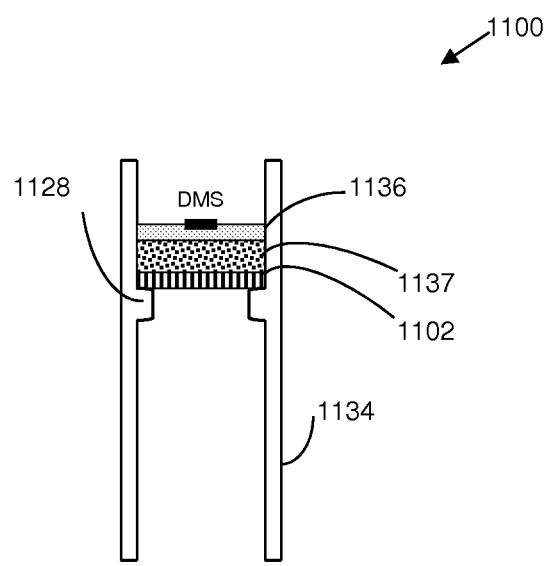
FIG. 14 is a cutaway partial front view of a plunger of a matrix spot processing device, in accordance with an embodiment.

FIG. 14 is a cutaway partial front view of a plunger 1134 of a matrix spot processing device 1100, in accordance with an embodiment.

The matrix spot processing device 1100 can be similar to other matrix spot processing devices described herein, for example, the matrix spot processing device 300 described with reference to FIG. 7, except that the matrix spot processing device 1100 includes a cleanup media 1137 positioned between a filtration media 1102 and an absorbent media 1136. The cleanup media 1137 can refer to a chromatographic sorbent or the like having properties related to hydrophilic, hydrophobic, ion-exchange, size exclusion, affinity, and so on. The cleanup media 1137 can include a device comprising packed-bed materials for sample cleanup, a chemical absorption media or the like, or a combination thereof. Other examples of a cleanup media 1137 can include but not be limited to an adsorptive media, affinity media, molecular-imprinted polymers, activated charcoal, or a combination thereof. Other examples of a cleanup media 1137 can include but not be limited to aliphatic chains, e.g., C-18, C-8, etc., aromatic groups, amines, sulfonates, acids, bases, diols, alcohols, amides, or a combination thereof. Sorbent materials can be constructed and arranged as, but not limited to, particles, spheres, granules, particulates, monoliths, gels, and so on. The selection of the type of cleanup sorbent to use can be based on the chemistry of what is desired to be removed from the sample extract. For example, different devices can be formed, each with one or more different types of sorbent.

The cleanup media 1137 enables a removal of one or more constituents of a liquid extract prior to or contemporaneously with the filtration media 1102 filtering the liquid extract.

For example, a user can spot a biological fluid on the absorbent media 1136, i.e., a DMS. The liquid extract passes through the cleanup media 1137 for removing constituents of the liquid extract such as phospholipids, and passes through the filtration media 1102 for removing particulates or other impurities having a particular size resulting in a filtered extract in a plunger reservoir or the like. The filtered extract can subsequently be analyzed in accordance with embodiments described herein.

A combination of the absorbent media 1136, the cleanup media 1137, and the filtration media 1102 can be positioned at a lip 1128, a mount or other related protrusion that extends from the inner wall of the plunger 1134. Alternatively, a combination of the absorbent media 1136, the cleanup media 1137, and the filtration media 1102 can be positioned in a groove, similar to the groove 28 described in FIG. 2, which has a predetermined dimension such as height to accommodate and hold in place the combination of the absorbent media 1136, the cleanup media 1137, and the filtration media 1102 about at least a portion of a perimeter of an inner sidewall of the plunger 1134.

Figure 15:
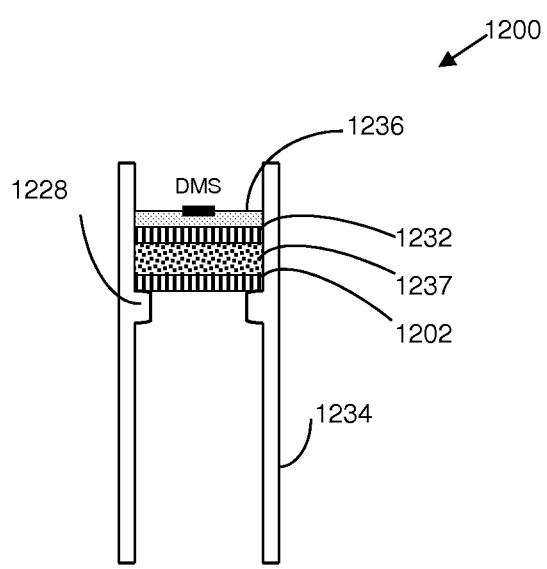
FIG. 15 is a cutaway partial front view of a plunger of a matrix spot processing device, in accordance with another embodiment.

FIG. 15 is a cutaway partial front view of a plunger 1234 of a matrix spot processing device 1200, in accordance with another embodiment.

The matrix spot processing device 1200 includes an absorbent media 1236, a first filter media 1232, a cleanup media 1237, and a second filter media 1202. In some embodiments, the first filter media 1232 and the second filter media 1202 are each constructed and arranged for different filtering purposes, for example, having different porosity or filtering capabilities. The cleanup media 1237 is at, for example, in contact with, the second filter media 1202. Accordingly, the cleanup media 1237 is sandwiched between the first filter media 1232 and the second filter media 1202. The first filter media 1232 and the second filter media 1202 can surround the cleanup media 1237 and provide a structure for the cleanup media 1237. The absorbent media 1236 is at, for example, in contact with, the first filter media 1232.

The second filter media 1202 can be positioned at a lip 1228, a mount or other related protrusion that extends from the inner wall of the plunger 1234. Alternatively, a stacking of the absorbent media 1236, the first filter media 1232, the cleanup media 1237, and the second filter media 1202 can be positioned in a groove, similar to the groove 28 described in FIG. 2, which has a predetermined dimension such as height to accommodate and hold in place the combination of the absorbent media 1236, the first filter media 1232, the cleanup media 1237, and the second filter media 1202 about at least a portion of a perimeter of an inner sidewall of the plunger 1234.

Figure 16:
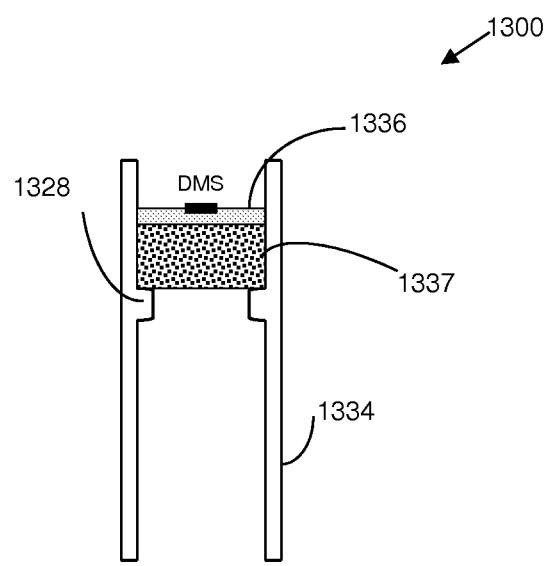
FIG. 16 is a cutaway partial front view of a plunger of a matrix spot processing device, in accordance with another embodiment.

FIG. 16 is a cutaway partial front view of a plunger 1334 of a matrix spot processing device 1300, in accordance with another embodiment. The matrix spot processing device 1300 includes an absorbent media 1336 and a one piece or unitary cleanup/filter media 1337 positioned on the absorbent media 1336. The cleanup/filter media 1337 performs one or more functions of a cleanup media described herein and can include one or more materials similar to or the same as a cleanup media described herein, and one or more filters. For example, the cleanup/filter media 1337 can include well-known chemical compositions that are capable of removing specific contaminants, for example, phospholipids. The one-piece media structure provides for simplified construction, and can be configured to reduce a holdup volume as compared to multiple media configurations. The cleanup/filter media 1337 can comprise a monolithic structure.

The cleanup/filter media 1337 can be positioned at a lip 1328, a mount or other related protrusion that extends from the inner wall of the plunger 1334. Alternatively, a combination of the absorbent media 1336 and the cleanup/filter media 1337 can be positioned in a groove, similar to the groove 28 described in FIG. 2, which has a predetermined dimension such as height to accommodate and hold in place the absorbent media 1336 and/or the cleanup/filter media 1337 about at least a portion of a perimeter of an inner sidewall of the plunger 1334.

Figure 17:
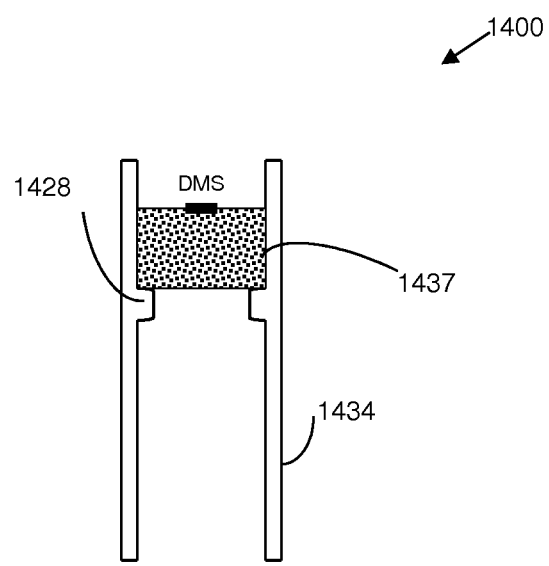
FIG. 17 is a cutaway partial front view of a plunger of a matrix spot processing device, in accordance with another embodiment.

FIG. 17 is a cutaway partial front view of a plunger 1434 of a matrix spot processing device 1400, in accordance with another embodiment.

The matrix spot processing device 1400 includes a one piece or unitary absorbent/cleanup/filter media 1437 positioned in a region of the plunger 1434. The absorbent/cleanup/filter media 1437 performs one or more functions of a cleanup media, for example, described herein, one or more filters and an absorbent media, for, example, described herein. Therefore, details are not repeated for reasons related to brevity.

The absorbent/cleanup/filter media 1437 can be positioned at a lip 1428, a mount or other related protrusion that extends from the inner wall of the plunger 1434. Alternatively, the absorbent/cleanup/filter media 1437 can be positioned in a groove, similar to the groove 28 described in FIG. 2, which has a predetermined dimension such as height to accommodate and hold in place the absorbent/cleanup/filter media 1437 about at least a portion of a perimeter of an inner sidewall of the plunger 1434.

While the invention has been shown and described with reference to specific embodiments, it should be understood by those skilled in the art that various changes in form and detail may be made therein without departing from the spirit and scope of the invention as recited in the accompanying claims. By way of examples, in embodiments of methods and systems described above, a solvent is used to extract components from a DBS or other form of sample. Generally, the extraction solvent is in the form of a liquid; however, in some embodiments, the extraction solvent may be a gas or a supercritical fluid. In other embodiments, the sample is provided in a solid form (e.g., a dried tissue sample) instead of a dried sample spot on a carrier. The solid sample does not need to be provided on a carrier and can, in some embodiments, be in a frozen state or be substantially dried. In other embodiments, non-biological fluids, for example, liquids, are provided with the devices described herein. One of ordinary skill in the art readily understands the type of samples, whether biological or non-biological, that can be applied in the various embodiments.

What is claimed is:

1. A matrix spot processing device, comprising:
   a plunger having a body containing a first reservoir extending between a first end and a second end;
   an absorbent media positioned on the first end of the plunger, wherein a blood sample is configured to be spotted on a first side of the absorbent media and wherein the first reservoir is located on a second side of the absorbent media; and
   an extraction solvent container including a second reservoir containing an extraction solvent,
   wherein the first end of the plunger is configured to be inserted into the extraction solvent container, wherein the plunger is configured to be compressed into the extraction solvent container such that the extraction solvent is transferred from the second reservoir through the absorbent media into the first reservoir to generate an extract from an interaction between the extraction solvent and the spotted sample at the absorbent media.

2. The matrix spot processing device of claim 1, wherein the sample includes a biological matrix.

3. The matrix spot processing device of claim 1, wherein the first region and the second region include a common region.

4. The matrix spot processing device of claim 1, further comprising an attachment mechanism at an inner sidewall at the reservoir of the tubular apparatus, wherein the absorbent media is coupled to the attachment mechanism.

5. The matrix spot processing device of claim 4, wherein the attachment mechanism includes a groove or a lip that about at least portion of a perimeter of the inner sidewall.

6. The matrix spot processing device of claim 1, wherein when a force is applied to at least one of the plunger and the extraction solvent container, a distance between the absorbent media and an end of the first region of the reservoir in the extraction solvent container is reduced such that at least a portion of the extraction solvent in the extraction solvent container interacts with the sample to form the extract at the second region of the reservoir.

7. The matrix spot processing device of claim 1, further comprising a support structure that couples a plurality of tubular apparatuses together in a predetermined arrangement, wherein the second regions of two or more tubular apparatuses are aligned along a common axis.

8. The matrix spot processing device of claim 7, wherein the support structure comprises:
   a sample side that exposes to a user an absorbent media in each of the tubular apparatuses;
   an extraction side opposite the sample side that exposes to the user the first regions of the tubular apparatuses; and
   a plurality of apertures, a tubular apparatus of the plurality of tubular apparatuses held in place in each aperture to receive a sample.

9. The matrix spot processing device of claim 1, further comprising a filtration media between the absorbent media and the second region of the reservoir, the filtration media filtering the extraction solvent after the interaction between the extraction solvent and the spotted sample.

10. The matrix spot processing device of claim 1, wherein a width of the second region of the reservoir is less than a width of a location of the absorbent media at the tubular apparatus.

11. The matrix spot processing device of claim 1, further comprising a cleanup media proximal the second region of the reservoir, the cleanup media removing one or more constituents of the extract prior to receipt of the extract at the second region of the reservoir.

12. The matrix spot processing device of claim 1, further comprising a filtration media, wherein the cleanup media is between the absorbent media and the filtration media.

13. The matrix spot processing device of claim 1, further comprising a first filter media and a second filter media, wherein the cleanup media is between the first filter media and a second filter media, and wherein the absorbent media is on the first filter media.

14. The matrix spot processing device of claim 1, further comprising a unitary cleanup/filter media positioned between the absorbent media and the reservoir in the tubular apparatus.

15. The matrix spot processing device of claim 1, further comprising a unitary absorbent/cleanup/filter media positioned in the tubular apparatus.

16. The matrix spot processing device of claim 1, wherein the sample includes a biological matrix.

17. The matrix spot processing device of claim 1, wherein the first region and the second region include a common region.

18. The matrix spot processing device of claim 1, further comprising an attachment mechanism at an inner sidewall at the reservoir of the tubular apparatus, wherein the absorbent media is coupled to the attachment mechanism.

19. The matrix spot processing device of claim 18, wherein the attachment mechanism includes a groove or a lip that about at least portion of a perimeter of the inner sidewall.

20. The matrix spot processing device of claim 1, wherein when a force is applied to at least one of the plunger and the container, a distance between the absorbent media and an end of the first region of the reservoir in the container is reduced such that at least a portion of the extraction solvent in the container interacts with the sample to form the extract at the second region of the reservoir.

21. The matrix spot processing device of claim 1, further comprising a support structure that couples a plurality of tubular apparatuses together in a predetermined arrangement, wherein the second regions of two or more tubular apparatuses are aligned along a common axis.

22. The matrix spot processing device of claim 21, wherein the support structure comprises:
   a sample side that exposes to a user an absorbent media in each of the tubular apparatuses;
   an extraction side opposite the sample side that exposes to the user the first regions of the tubular apparatuses; and
   a plurality of apertures, a tubular apparatus of the plurality of tubular apparatuses held in place in each aperture to receive a sample.

23. The matrix spot processing device of claim 1, further comprising a filtration media between the absorbent media and the second region of the reservoir, the filtration media filtering the extraction solvent after the interaction between the extraction solvent and the spotted sample.

24. The matrix spot processing device of claim 1, wherein a width of the second region of the reservoir is less than a width of a location of the absorbent media at the tubular apparatus.

25. The matrix spot processing device of claim 1, further comprising a cleanup media proximal the second region of the reservoir, the cleanup media removing one or more constituents of the extract prior to receipt of the extract at the second region of the reservoir.

26. The matrix spot processing device of claim 1, further comprising a filtration media, wherein the cleanup media is between the absorbent media and the filtration media.

27. The matrix spot processing device of claim 1, further comprising a first filter media and a second filter media, wherein the cleanup media is between the first filter media and a second filter media, and wherein the absorbent media is on the first filter media.

28. The matrix spot processing device of claim 1, further comprising a unitary cleanup/filter media positioned between the absorbent media and the reservoir in the tubular apparatus.

29. The matrix spot processing device of claim 1, further comprising a unitary absorbent/cleanup/filter media positioned in the tubular apparatus.

30. The matrix spot processing device of claim 1, further comprising a septum located at the second end of the plunger, wherein the septum is configured to allow for withdrawing the extract from the first reservoir.

31. The matrix spot processing device of claim 1, wherein the plunger further comprises a removable cap and wherein the septum is located on the removable cap.

32. The matrix spot processing device of claim 1, wherein the plunger further comprises a first seal located on an outer surface of the body proximate the first end and a second seal located on the outer surface proximate the second end.

33. The matrix spot processing device of claim 32, wherein the first seal is configured to provide a fluid tight seal between the outer surface of the body and an inner surface of the extraction solvent container.

34. The matrix spot processing device of claim 1, wherein the plunger further comprises a first seal located on an outer surface of the body proximate the first end and wherein the first seal is configured to provide a fluid tight seal between the outer surface of the body and an inner surface of the extraction solvent container.

35. The matrix spot processing device of claim 34, wherein the first seal is configured to create a pressure in the extraction solvent container when the plunger is inserted into the extraction solvent container, wherein the pressure is configured to cause at least some of the extraction solvent to be transferred from the second reservoir through the absorbent media into the first reservoir.

36. The matrix spot processing device of claim 1, wherein the absorbent media is exposed to an exterior of the matrix spot processing device such that the absorbent media is configured to receive the spotted blood sample.

\* \* \* \* \*